US006976977B2

(12) United States Patent
Yam

(10) Patent No.: US 6,976,977 B2
(45) Date of Patent: Dec. 20, 2005

(54) VACUUM SETTING AND INDICATION SYSTEM FOR A DRAINAGE DEVICE

(75) Inventor: Jacky Yam, St. Louis, MO (US)

(73) Assignee: Sherwood Services AG, Schaffhausen (CH)

(*) Notice: Subject to any disclaimer, the term of this patent is extended or adjusted under 35 U.S.C. 154(b) by 380 days.

(21) Appl. No.: 10/008,127

(22) Filed: Nov. 5, 2001

(65) Prior Publication Data

US 2002/0082568 A1    Jun. 27, 2002

Related U.S. Application Data

(60) Provisional application No. 60/251,724, filed on Dec. 6, 2000.

(51) Int. Cl.⁷ .............................................. A61M 1/00
(52) U.S. Cl. ..................... 604/320; 604/320; 604/118; 74/553; 73/714; 73/866.3
(58) Field of Search ................. 604/319–321, 604/118–119; 74/553; 73/866.3; 16/110.1, 16/414, 417, 430, 433, 441

(56) References Cited

U.S. PATENT DOCUMENTS

| | | | |
|---|---|---|---|
| 1,513,925 A * | 11/1924 | Murdock ........................ 403/6 |
| 3,998,227 A * | 12/1976 | Holbrook et al. ........... 604/119 |
| 4,031,847 A | 6/1977 | Sullivan ....................... 116/65 |
| 4,372,336 A | 2/1983 | Cornell et al. |
| 4,396,386 A | 8/1983 | Kurtz et al. |
| 4,468,226 A | 8/1984 | Kurtz et al. |
| 4,519,796 A | 5/1985 | Russo |
| 4,550,749 A | 11/1985 | Krikorian |
| 4,605,400 A | 8/1986 | Kurtz et al. |
| 4,648,870 A | 3/1987 | Goldberg et al. ........... 604/135 |
| 4,655,754 A * | 4/1987 | Richmond et al. .......... 604/323 |
| 4,675,011 A | 6/1987 | Kurtz et al. |
| 4,738,671 A | 4/1988 | Elliott et al. |
| 4,747,843 A | 5/1988 | Felix et al. |
| 4,747,844 A | 5/1988 | Elliott |
| 4,784,642 A | 11/1988 | Everett, Jr. et al. |
| 4,883,476 A | 11/1989 | Kurtz et al. |
| 4,898,593 A | 2/1990 | Swisher et al. |
| 4,911,697 A * | 3/1990 | Kerwin ........................ 604/318 |
| 5,073,172 A * | 12/1991 | Fell ............................. 604/319 |
| 5,114,416 A | 5/1992 | Karwoski et al. |
| 5,236,425 A | 8/1993 | Kurtz et al. |
| 5,279,550 A | 1/1994 | Habib et al. ................... 604/38 |
| 5,421,808 A | 6/1995 | Osbon et al. .................. 600/38 |
| 5,507,734 A | 4/1996 | Everett, Jr. et al. |
| 5,842,764 A * | 12/1998 | Berardi ........................ 362/23 |

(Continued)

FOREIGN PATENT DOCUMENTS

DE        3107974 A1      3/1981

(Continued)

Primary Examiner—Larry I. Schwartz
Assistant Examiner—Ginger Chapman
(74) Attorney, Agent, or Firm—Greensfelder Hemker & Gale PC

(57) ABSTRACT

A drainage device comprising an improved vacuum regulator assembly is disclosed which includes an adjustable knob for indicating the degree of vacuum being applied to the device from a number of incident viewing angles. Similarly, a vacuum indicator assembly is provided for indicating the presence or absence of vacuum being applied to drainage device. The indicator assembly provides an indication of vacuum inside drainage device from many viewing angles and includes a base defining a recess having a slanted surface with a vacuum symbol which is selectively masked by a collapsible thimble when vacuum is applied or removed from the drainage device.

27 Claims, 8 Drawing Sheets

U.S. PATENT DOCUMENTS

| | | | |
|---|---|---|---|
| 5,865,408 A * | 2/1999 | Swisher et al. | 248/188.1 |
| 5,925,025 A | 7/1999 | Wailbacher et al. | |
| 6,042,560 A | 3/2000 | Niederberger | 604/74 |
| 6,052,929 A | 4/2000 | Canadas | 40/331 |
| 6,112,619 A * | 9/2000 | Campbell | 74/553 |
| 6,346,096 B1 * | 2/2002 | Yam et al. | 604/321 |
| 6,481,986 B1 * | 11/2002 | Silver et al. | 417/441 |
| 6,632,203 B2 * | 10/2003 | Swisher et al. | 604/317 |
| 6,659,987 B2 * | 12/2003 | Swisher et al. | 604/319 |

FOREIGN PATENT DOCUMENTS

| | | |
|---|---|---|
| DE | 3828991 A1 | 8/1988 |
| EP | 0 438 703 A1 | 7/1991 |
| GB | 868992 | 5/1961 |
| WO | WO 93/02627 | 7/1992 |

\* cited by examiner

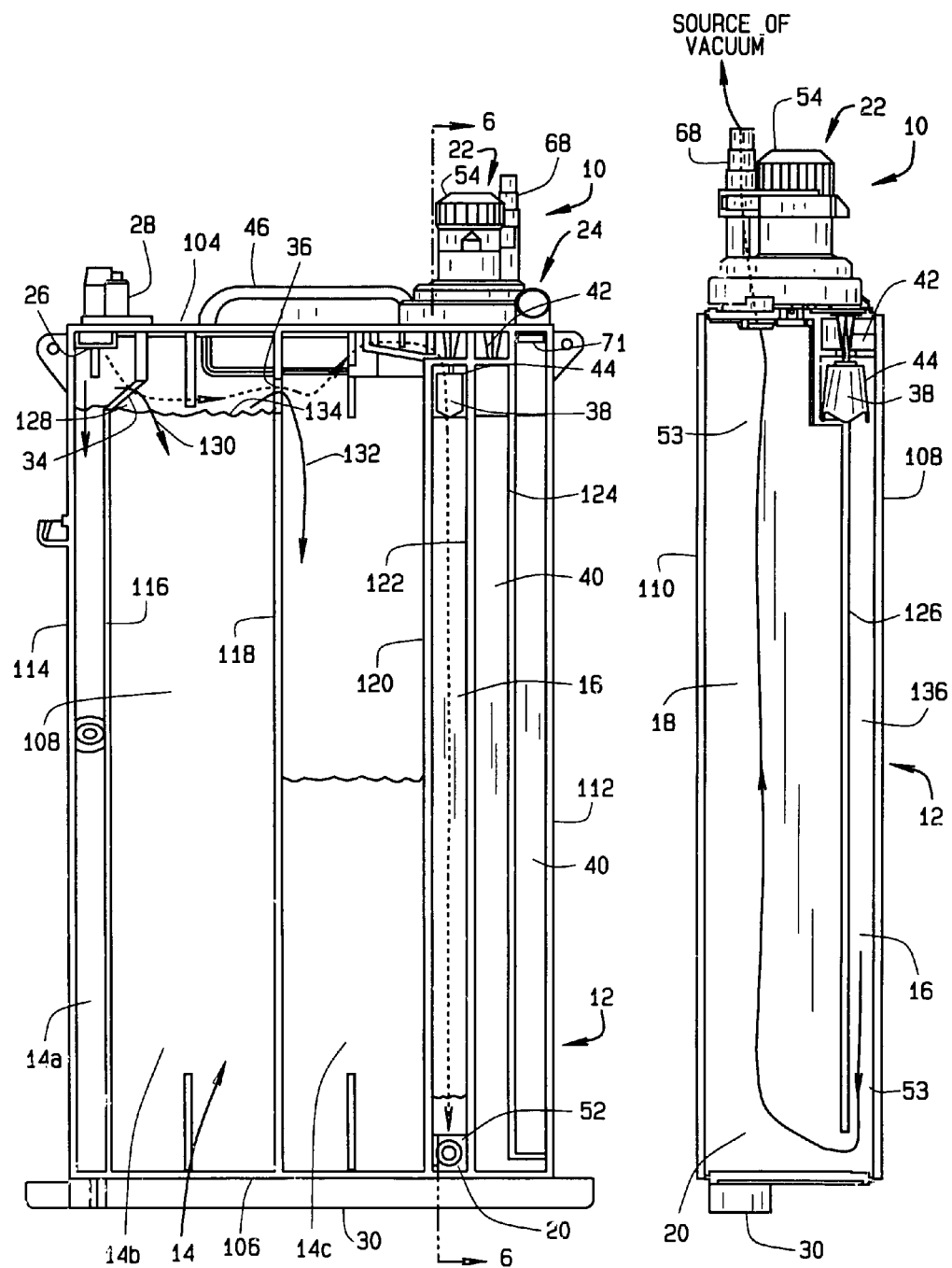

US 6,976,977 B2

VACUUM SETTING AND INDICATION SYSTEM FOR A DRAINAGE DEVICE

CROSS-REFERENCE TO RELATED APPLICATION

This application claims benefit of U.S. Provisional Application No. 60/251,724, filed Dec. 6, 2000.

BACKGROUND OF THE INVENTION

1. Field of the Invention

The present invention relates to a chest drainage system, and particularly to a dry chest drainage apparatus for suctioning gases and liquids from the chest cavity of a patient. More specifically, the present invention relates to a vacuum setting and indication system for a dry chest drainage apparatus which permits viewing by the user from a number of directions.

2. Prior Art

A chest drainage device is an apparatus for suctioning gases and liquids from the pleural cavity of patients. The pleural cavity lies within the rib cage above the diaphragm and is surrounded by the pleural membrane. The pleural cavity contains both lungs, which in their normal expanded state fill the pleural cavity. Several conditions and diseases such as interventional surgery, trauma, emphysema and various respiratory infections can cause build up of liquid and gases around the lungs in the intrapleural space. When this happens, it causes the lungs to collapse to a volume much less than that of the pleural cavity, thereby severely impairing the breathing functions of the patient. The lungs can be re-expanded to their normal state to fill the pleural cavity by draining the liquid and gases from the intrepleural space using a chest drainage device.

There are many kinds of chest drainage devices used to drain the intrapleural space of a patient. One kind of drainage device, sometimes referred to as a "three-bottle" type, is illustrated in U.S. Pat. No. 3,363,626 to Bidwell et al. entitled "Underwater Drainage Apparatus". The "three-bottle" type drainage device has three interconnecting chambers which comprise: (1) a collection chamber for collecting liquids and gases suctioned from the patient's pleural cavity; (2) an underwater seal chamber which communicates with the collection chamber and has a water seal which acts as a one way valve for passing gases from the patient's pleural cavity to the atmosphere; and (3) a suction control chamber for limiting the maximum suction (or negative pressure) applied to the patient's pleural cavity.

Another kind of drainage device is the "four-bottle system" which includes the three chambers of the "three-bottle system" and adds a fourth chamber, referred to as a manometer chamber, which provides an accurate indicia of the level of suction being applied to the cavity to be drained. However, the "four-bottle system" suffers from several deficiencies. In particular, the suction control chamber is noisy due to bubbling of atmospheric air through the liquid maintained therein; and the system is somewhat bulky.

With increased awareness of the anxiety-provoking nature of noise in the hospital environment, a mechanical regulator to adjust the level of vacuum applied was provided as a substitute for a liquid filled suction control chamber of the prior art. U.S. Pat. No. 4,372,336 to Cornell discloses a mechanical regulator for a drainage device having a liquid-filled manometer chamber which provides a visual indication of the vacuum level present in the device. Although the drainage device of Cornell is an improvement over prior art drainage devices, such devices could still be further improved. For example a drainage device having a dry system containing no liquid in either the suction control chamber or manometer chamber would be desirable.

Drainage devices employing a dry system for draining liquid and gases from a patient's pleural cavity use a mechanical regulator to both adjust the level of vacuum to the device as well as a means of indicating the actual degree of vacuum being applied to the drainage device. Such drainage devices normally have a dial or knob disposed along either the side or front wall of the drainage device casing for adjusting the degree of vacuum by rotating the dial or knob in one direction. U.S. Pat. No. 4,784,642 to Everett, Jr., et al. and U.S. Pat. No. 5,989,234 to Valerio, et al. are illustrative of drainage devices using a mechanical regulator in the form of a rotatable dial or knob on the front or side of the device to adjust the level of vacuum in the device. However, such prior art adjustment means are difficult to view from different angles and are cumbersome to operate since these mechanisms have mechanical arrangements that can become stuck or require extra effort to operate, while the vacuum setting indicia surrounding the knob dial can only be viewed from the front or side of the device.

Some drainage devices are also provided with a vacuum indicator assembly to visually indicate the presence of vacuum inside the drainage device. Vacuum indicator assemblies can be in the form of an extendable baffle, a floating ball chamber or an inflatable masking diaphragm which provides a selective visual signal to the user of proper vacuum in the drainage device. Similar to the vacuum indicator assembly disclosed in U.S. Pat. No. 4,747,843 to Felix et al., vacuum indicator assemblies of the prior art are recessed along the front or top portions of the drainage device, thereby making them strictly viewable from a limited angle.

The drawback of having either the vacuum indicator assembly or vacuum setting indicia being recessed inside the drainage device along either the side or top portion thereof is that a user may not be able to clearly view either the indicator assembly or setting indicia when the drainage device is placed on the floor or a desk, or suspended from a pole. In other words, when the drainage device is placed on the floor, the user cannot view the vacuum indicator assembly if the assembly is located along the side of the device, and thereby hidden from view.

Therefore, there is a need in the art for a drainage device having a mechanical regulator which gives a clear indication of the vacuum level setting to the user from a number of angles. There is a further need in the art for a drainage device having a vacuum indicator assembly that is clearly viewable from many directions by the user.

OBJECTS AND SUMMARY OF THE INVENTION

One feature of the present invention is to provide a control knob for a mechanical regulator of a drainage device having vacuum setting indicia that is viewable from a number of angles.

Another feature of the present invention is to provide a drainage device having a vacuum indicator assembly that is viewable from more than one direction.

A further feature of the present invention is to provide a drainage device having vacuum setting indicia that includes a raised marker.

Yet another feature of the present invention is to provide a drainage device having vacuum setting indicia placed along a slanted surface.

Another further feature of the present invention is to provide a drainage device having a vacuum indicator assembly that is raised above the casing of the device.

In brief summary, the present invention overcomes and substantially alleviates the deficiencies present in the art by providing a vacuum setting and indication system for a waterless drainage device having a vacuum setting indicia and a vacuum indicator assembly which are viewable from a number of directions.

Preferably, the drainage device comprises a unitary casing having a collection chamber for the collection of liquids and gases, a water seal chamber for preventing evacuated gases from reentering the collection chamber, and a mechanical regulator for regulating the degree of vacuum inside the drainage device. The collection chamber is in fluid flow communication with a patient's pleural cavity through a catheter having one end disposed therein and the other end attached to a collection port of the collection chamber. The water seal chamber defines a compartment having one end in communication with the collection chamber and the other end in communication with a source of vacuum. A water seal is disposed at the bottom of the water seal chamber and prevents the reflux of evacuated gases back into the collection chamber during a sudden high negative pressure condition in the collection chamber, for example, when a patient takes a quick and deep inhalation.

The mechanical regulator is preferably a single stage regulator which includes a housing that encloses a suction regulating chamber. The housing further includes a regulator control knob which operates to adjust the level of vacuum applied to the drainage device. According to one aspect of the present invention, the control knob has a slanted surface having a plurality of vacuum setting levels printed thereon which are viewable from either the top or sides of the drainage device. The control knob further includes a textured arrow which illustrates the direction the knob is turned in order to increase the level of vacuum and a raised marking arrow for indicating the exact degree of vacuum being applied to the drainage device.

The drainage device further includes a vacuum indicator assembly for giving the user a visual indication of the presence of vacuum in the device. The vacuum indicator assembly comprises a base attached to the top portion of the drainage device in communication with the collection chamber with the base defining a raised tubular member which extends upwardly from the base. The free end of the raised tubular member defines a recess having a slanted surface with an arrow or other appropriate vacuum symbol marked thereon for indicating the presence of vacuum in the drainage device when visible and an aperture which is in fluid flow communication with the vacuum from the collection chamber. The vacuum indicator assembly further comprises a semi-transparent, flexible thimble which encases the raised tubular member in a fluid tight seal such that the thimble is placed in an inflated condition when vacuum is not present within the drainage device or in a deflated condition when vacuum is present within the device. In the inflated condition with no vacuum applied to the drainage device, the thimble masks the slanted surface such that the vacuum symbol is hidden from view, while in the deflated condition the flexible thimble collapses onto the slanted surface and exposes the vacuum symbol to view, thereby indicating the presence of vacuum in the drainage device to the user. Finally, a casing houses the thimble and base so that the vacuum indicator assembly is properly oriented relative to the drainage device.

These and other objects of the present invention are realized in the preferred embodiment, described by way of example and not by way of limitation, which provides for a dry drainage device with a vacuum setting and indication system viewable from a number of directions.

Additional objects, advantages and novel features of the invention will be set forth in the description which follows, and will become apparent to those skilled in the art upon examination of the following more detailed description and drawings in which like elements of the invention are similarly numbered throughout.

BRIEF DESCRIPTION OF THE DRAWINGS

FIG. 5 is a front view of the drainage device illustrating the liquid and air flow pathways according to the present invention;

FIG. 6 is a cross sectional view of the drainage device, taken along line 6—6 of FIG. 5, illustrating the air flow pathway to a vacuum source according to the present invention;

DETAILED DESCRIPTION OF THE INVENTION

Figure 1:
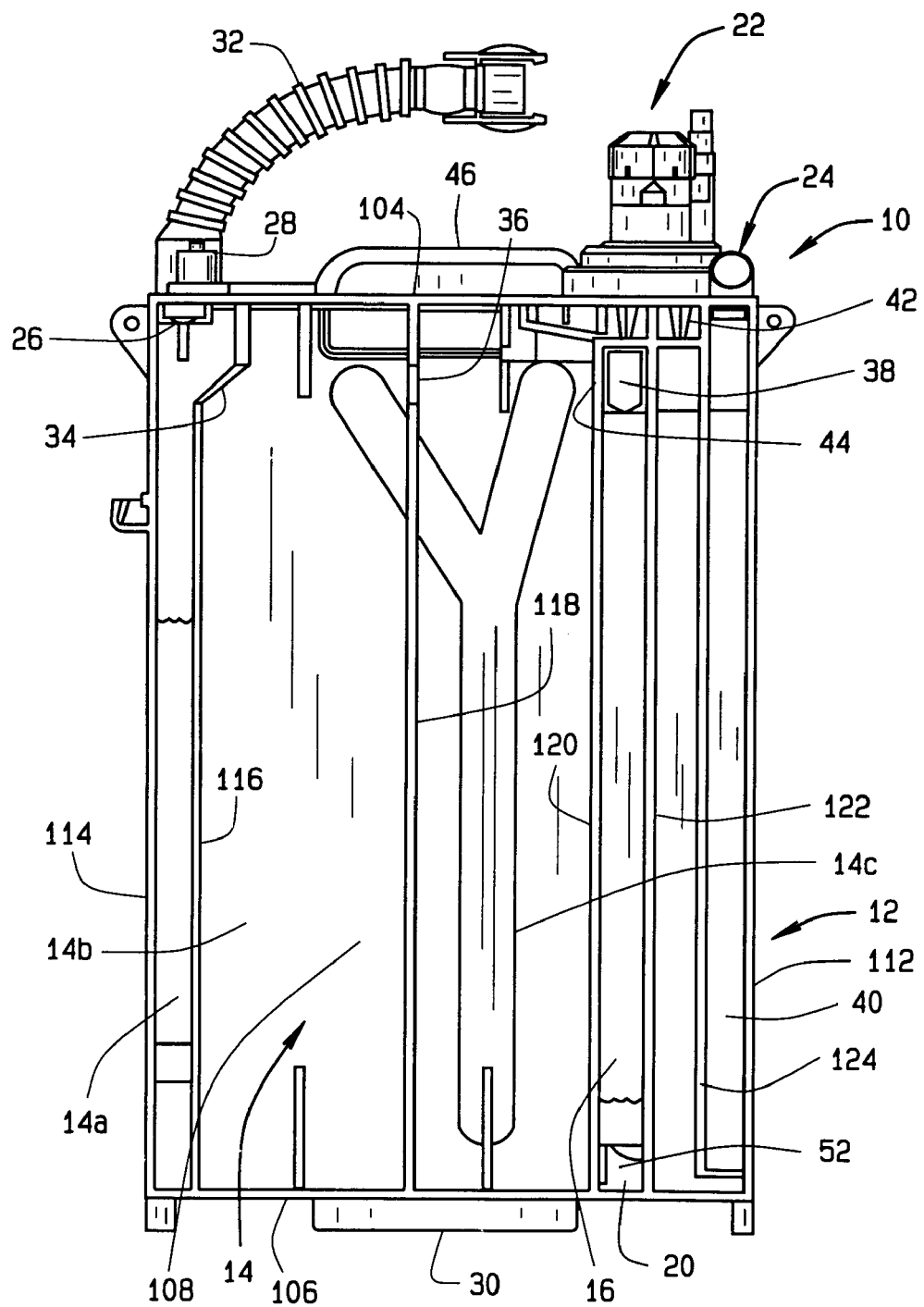
FIG. 1 is a front view of the drainage device according to the present invention.
Figure 4:
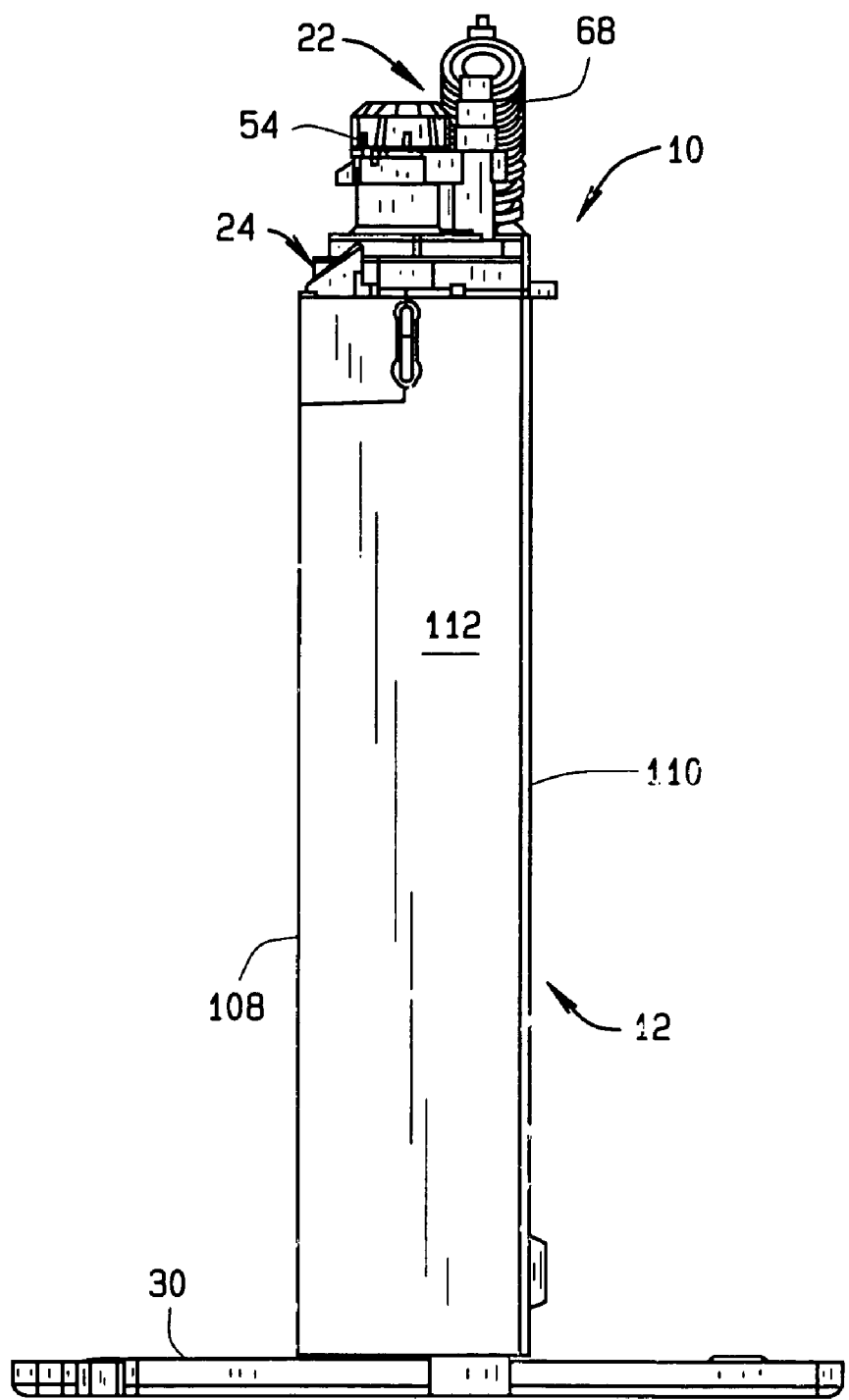
FIG. 4 is a side view of the drainage device according to the present invention.

Referring to the drawings, the preferred embodiment of the drainage device of the present invention is illustrated and generally indicated as 10 in FIG. 1. Drainage device 10 comprises a casing 12 having a top wall 104, a bottom wall 106, front and rear walls 108 and 110 (FIG. 4), respectively, and end walls 112 and 114. Casing 12 further comprises a collection chamber 14 for the collection of fluids, a water seal chamber 16 for preventing reflux of evacuated gases back into collection chamber 14, and a suction control chamber 18 in communication with a vacuum regulator assembly 22 for regulating the degree of vacuum inside drainage device 10. As shown, casing 12 also comprises interior partitions 116, 118, 120, 122, and 124 (FIG. 1) which are parallel to end walls 112 and 114, and a partition 126, which is parallel to front and rear walls 108 and 110, that divide the interior of casing 12 into collection chamber 14, water seal chamber 16, suction control chamber 18 as well as a number of other chambers and compartments as shall be discussed in greater detail below.

The top wall 104 of drainage device 10 comprises a negative pressure relief valve 28 for venting excess negative pressure from within casing 12, a collection port 26 for attachment to infusion tubing 32, vacuum regulator assembly 22 for the mechanical regulation of vacuum inside drainage device 10, and a vacuum indicator assembly 24 for giving a visual indication to the user of proper vacuum being applied to collection chamber 14. A handle 46 is also provided along top wall 104 for handling and transporting drainage device 10, while a rotatable stand 30 is attached to bottom wall 106 for providing a stable platform for drainage device.

With reference to collection chamber 14, partitions 116 and 118 divide collection chamber 14 into compartments 14a, 14b and 14c, to facilitate periodic monitoring of the level of liquid collected from a patient's cavity. As shown by arrows 128, 130 and 132 in FIG. 5, vacuum applied to drainage device 10 forces blood and other liquid 134 from the patient's chest cavity into compartment 14a through collection port 26 via patient tubing 32. When compartment 14a is filled to capacity, the liquid 134 will overflow through port 34 and into compartment 14b until that compartment is filled. Once compartment 14b is filled to capacity, any additional liquid 134 will overflow through port 36 and drop into compartment 14c. The present invention contemplates the use of appropriate indicia (not shown) marked along front wall 108 for each compartment 14a, 14b and 14c for providing a clear visual indication of the level of liquid being deposited in each respective compartment.

As best illustrated in FIGS. 5 and 6, once fluid from a patient's cavity is deposited inside collection chamber 14, gases are evacuated through the water seal chamber 16. Water seal chamber 16 prevents reflux of gases back to the patient by preventing the reentry of such gases into the collection chamber 14 using a buoyant valve 38 in combination with a water seal 20. The structure and operation of the buoyant valve 38 is disclosed in U.S. Pat. No. 4,372,336 to Cornell et al., entitled "Chest Drainage Unit With Controlled Automatic Excess Negativity Relief Feature" which has been incorporated by reference in its entirety. The water seal chamber 16 comprises a compartment 136 having upper and lower portions with the upper portion housing valve 38 and the lower portion having water seal 20 disposed therein. The lower portion of compartment 136 communicates with the lower portion of the suction control chamber 18 which is separated from compartment 136 by partition 126. As gases pass through the water seal 20 from collection chamber 14, the gases are evacuated from drainage device 10 through vacuum regulator assembly 22 to a vacuum source (not shown).

As further shown, vacuum regulator assembly 22 provides a means for regulating the degree of vacuum, venting of excess positive pressure, and a pathway for evacuating gases from drainage device 10. The basic operation of vacuum regulator assembly 22 is disclosed in U.S. Pat. No. 4,911,697 to Kerwin and is herein incorporated by reference in its entirety. Preferably, vacuum regulator assembly 22 comprises a positive pressure relief valve (not shown) for venting excess positive pressure generated inside collection chamber 14 and a vacuum port 68 for communicating with a source of vacuum. Both the positive pressure relief valve and vacuum port 68 communicate with a suction control chamber 18 that is in fluid flow communication with water seal 20. As illustrated in FIG. 6, arrow 53 represents the flow of evacuated gas from the collection chamber 14 and through water seal 20. Once the gas passes through water seal 20 it is evacuated from the suction control chamber 18 through the vacuum port 68 to the vacuum source.

Figure 7:
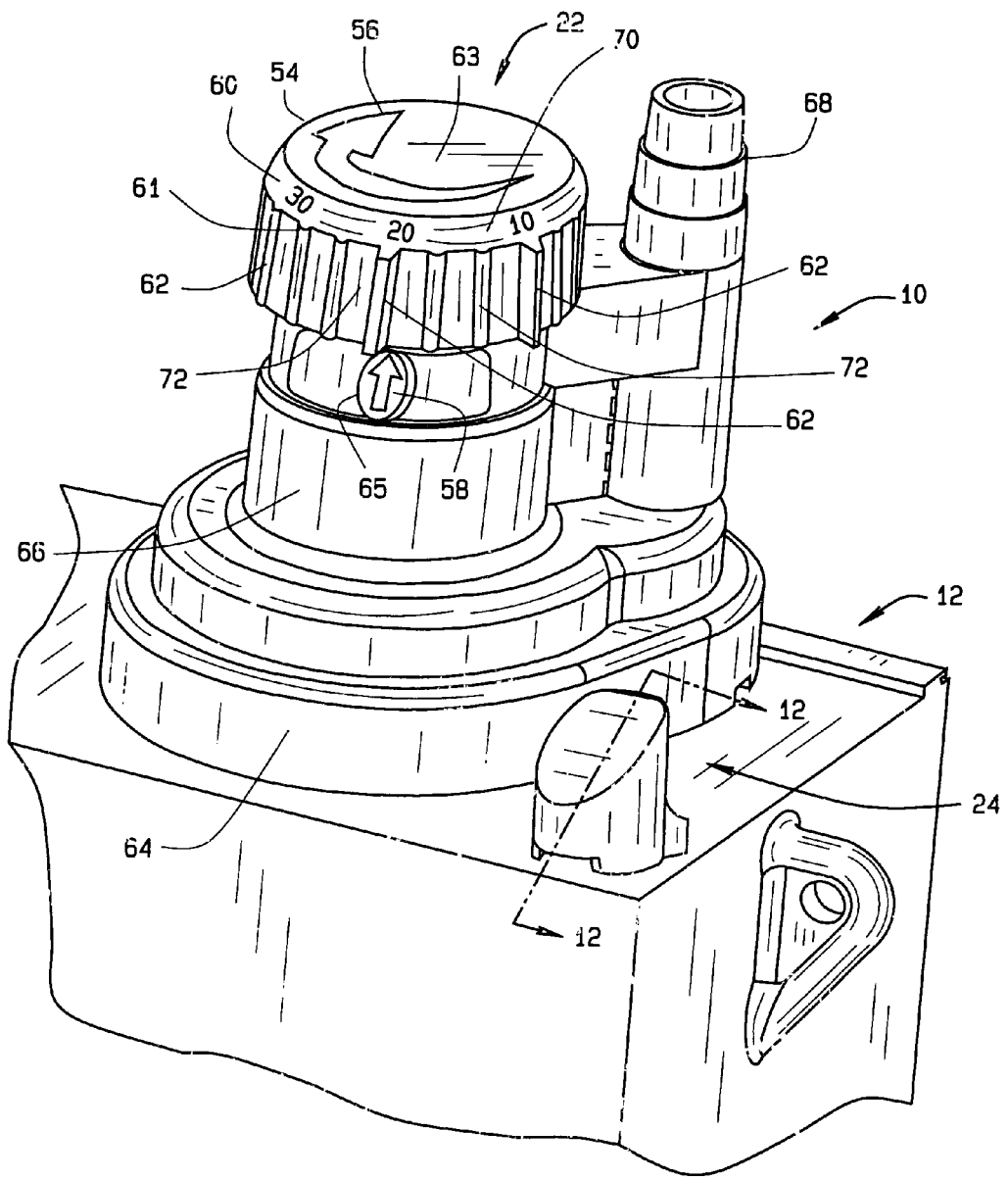
FIG. 7 is an enlarged perspective view of a vacuum regulator assembly and a vacuum indicator assembly according to the present invention.

Referring to FIG. 7, vacuum regulator assembly further comprises an adjustable knob 54 for controlling the degree of vacuum applied to drainage device 10. One unique aspect of the present invention is that knob 54 has a slanted surface 70 which is formed adjacent an annular shaped skirt 61 having a knurled portion 72 with ribs 62 interposed therebetween. As further shown, vacuum regulator assembly 22 comprises a base 64 seated on top wall 104 and a foundation 66 formed adjacent base 64 which seats knob 54 in rotatable engagement. Slanted surface 70 includes vacuum setting indicia 60, for example numerals, which gives the user a visual indication as to the degree of vacuum being applied to drainage device 10. As shall be appreciated by one of skill in the art, the configuration of slanted surface 70 permits a user to view vacuum setting indicia 60 from the top and all sides of drainage device 10 regardless of whether the device 10 is placed on the floor, alongside a patient, or suspended from a pole. A marking arrow 58 is formed on a slanted raised portion 65 which is provided directly below skirt 61 for indicating the exact degree of vacuum being indicated by vacuum setting indicia 60. The configuration of the slanted raised portion 65 also allows the user to view the marking arrow 58 from many directions. As further shown, a top portion 63 is provided adjacent slanted surface 70 and includes a raised indication arrow 56 which gives the user a visual indication as to the proper direction of increased vacuum when rotating knob 54. Preferably, the user rotates knob 54 in a clockwise direction for increasing vacuum and a counter-clockwise direction for decreasing vacuum; however, in the alternative an increase in vacuum may be made by rotating knob 54 in a reverse direction. Collectively, the vacuum setting indicia 60 on slanted surface 70 in combination with the marker arrow 58 on raised portion 65 permit the user to view the actual vacuum setting from either the top (FIG. 2) or the side (FIGS. 1, 3 and 4) of drainage device 10 regardless of where device 10 is placed relative to the user.

Figure 8:
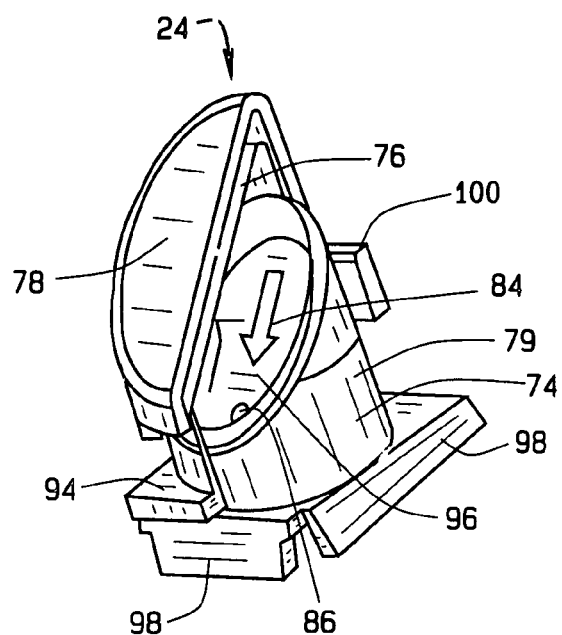
FIG. 8 is a partial cut-off view of the vacuum indicator assembly according to the present invention.
Figure 11:
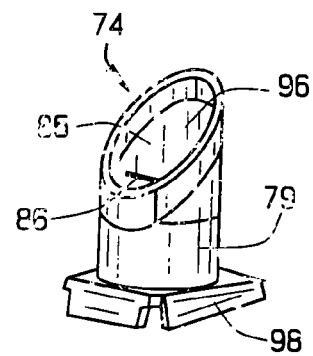
FIG. 11 is a perspective view of a base of the vacuum indicator assembly according to the present invention.
Figure 12:
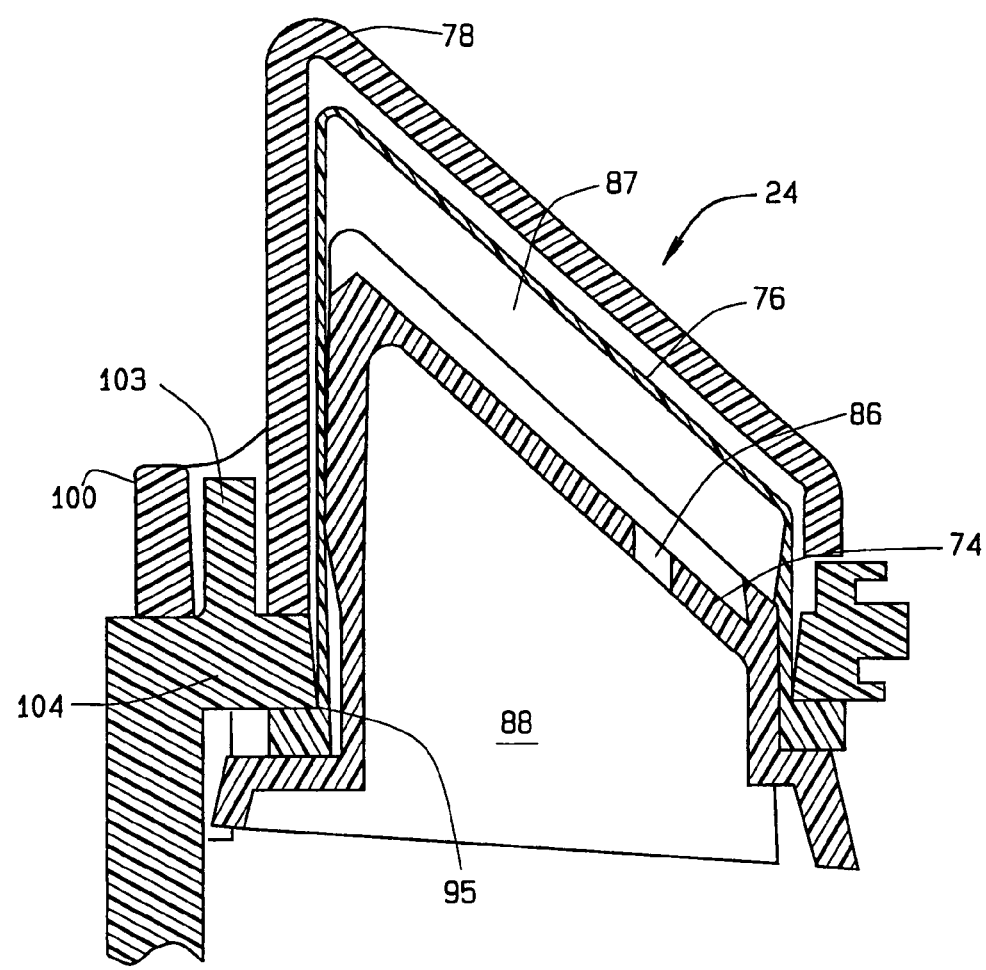
FIG. 12 is a cross sectional view of the vacuum indicator assembly, taken along line 12—12 of FIG. 7, according to the present invention.

Another aspect of the present invention is the provision for providing a visual indication of vacuum being applied to drainage device 10 that is visible to the user from a number of directions. Referring to FIGS. 8, 11 and 12, vacuum indicator assembly 24 comprises a raised base 74 defining a tubular-shaped extension member 79 forming a recess 85 at the free end of member 79 in communication with an internal chamber 88. Recess 85 comprises a slanted surface 96 which includes a vacuum symbol 84 marked thereon for indicating the presence of vacuum inside drainage device 10 and a hole 86 for establishing fluid flow communication between vacuum indicator assembly 24 and collection chamber 14. Because slanted surface 96 is formed at approximately a 45 degree angle relative to top wall 104, the user may easily view vacuum symbol from either the front, top or side of drainage device 10 when vacuum is present in collection chamber 14 as shall be explained in greater detail below. Base 74 further defines an insert portion 98 formed adjacent extension member 79 which is sized and shaped to engage an aperture 71 (FIG. 5) having a peripheral edge 95 formed through top wall 104 of casing 12. As further illustrated in FIG. 5, aperture 71 communicates with one end of a U-shaped passageway 40 through chamber 88, while the other end of passageway 40 communicates with collection chamber 14 through a flow chamber 42 which houses valve 38.

Figure 10:
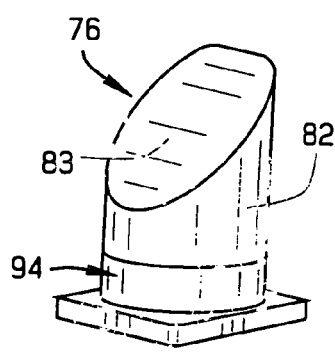
FIG. 10 is a perspective view of a thimble of the vacuum indicator assembly according to the present invention.

Referring to FIGS. 8 and 10, vacuum indicator assembly 24 further comprises a semi-transparent, collapsible thimble 76 which is sized and shaped to snuggly fit over extension member 79 and a protective cover 78 for encasing the thimble 76 and base 74. As shown specifically in FIG. 10, thimble 76 comprises a body 82 defining a slanted surface 83 at one end and a flange 94 at the other end thereof. When thimble 76 is properly engaged over base 74, a pocket 87 is formed between thimble 76 and recess 85 which is in fluid flow communication with collection chamber 14 through hole 86. Thimble 76 further defines a section 94 having increased thickness relative to the remainder of thimble 76. When the vacuum indicator assembly 24 is properly assembled, the peripheral edge 95 of aperture 71 abuts section 94 of thimble 76 against base 74 such that a fluid tight seal is established.

Figure 2:
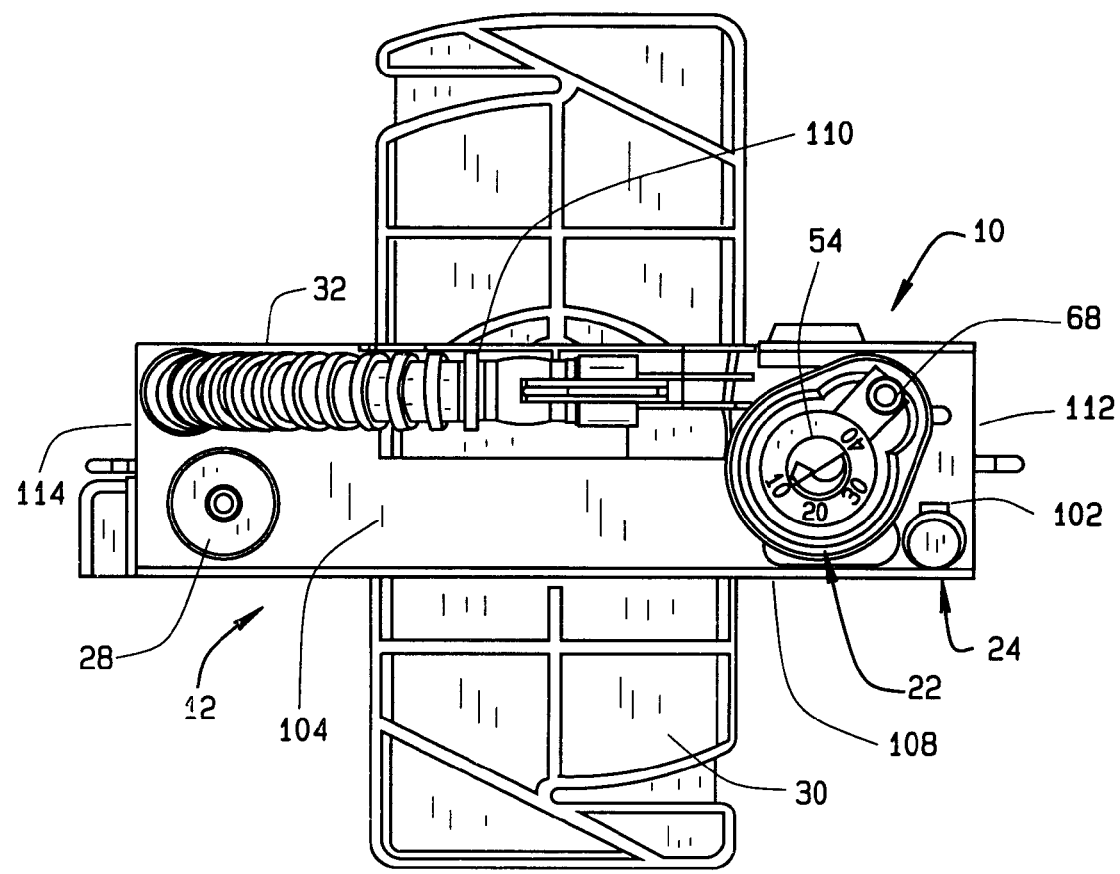
FIG. 2 is a top view of the drainage device according to the present invention.
Figure 9:
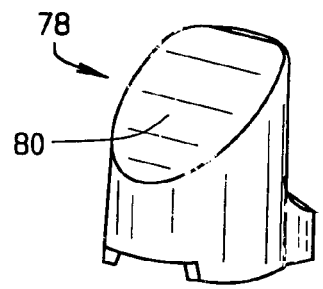
FIG. 9 is a perspective view of a cover of the vacuum indicator assembly according to the present invention.

Referring to FIGS. 2, 9 and 12, protective cover 78 has a beveled surface 80 which is shaped substantially similar in configuration to thimble 76. Cover 78 further includes an alignment member 100 defining an opening 102 which engages a raised extension 103 extending outwardly from top wall 104. When vacuum indicator assembly 24 is properly aligned by alignment member 100, vacuum symbol 84 is viewable by the user from either the top or sides of drainage device 10. Preferably, cover 78 is made of polystyrene, the thimble of silicone, and the base of polypropylene, although any suitable medical grade material is felt to fall within the scope of the present invention.

In operation, vacuum indicator assembly 24 exposes vacuum symbol 84 to view whenever vacuum is present within the collection chamber 14. Because of the free communication between the pocket 87 of vacuum indicator assembly 24 and the collection chamber 14, the same degree of vacuum present within the collection chamber 14 will also be present inside pocket 87. Accordingly, the vacuum present within pocket 87 causes the portion of thimble 76 covering recess 85 to deflate and collapse over recess 85, thereby exposing vacuum symbol 84 to view by the user through the semi-transparent material of thimble 76. Conversely, when no vacuum is present within the collection chamber 14 thimble 76 is caused to inflate and mask vacuum symbol 84 from view.

Figure 3:
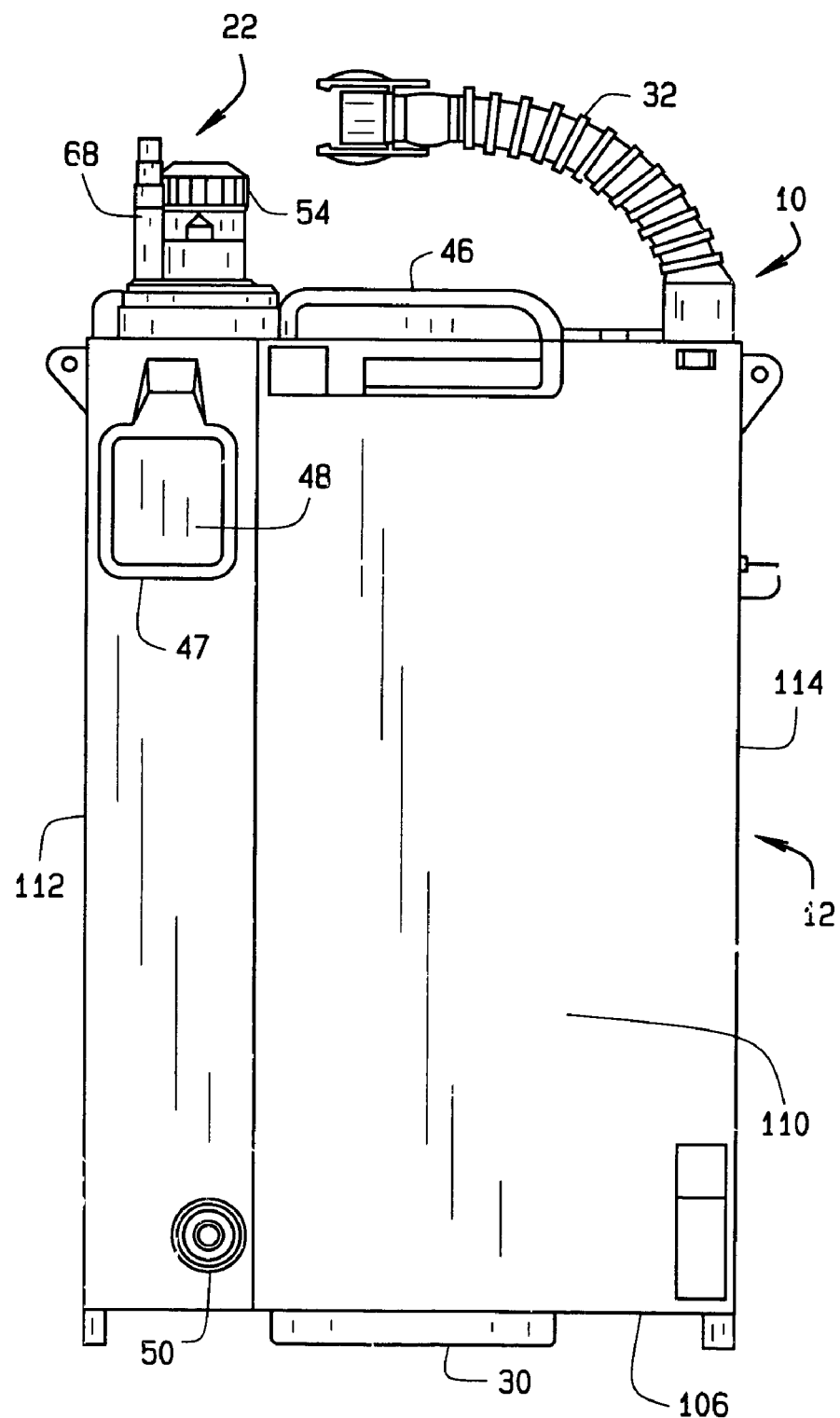
FIG. 3 is a back view of the drainage device according to the present invention.

Referring to FIG. 3, rear wall 100 defines an aperture 47 in fluid flow communication with suction control chamber 18. According to one aspect of the present invention, a rotatable fill spout 48 covers aperture 47 and provides a means for filling the water seal chamber 16 with water for forming water seal 20. Another aspect of the present invention is the provision for a water seal access port 50 (FIG. 3) having a mechanical one way valve (not shown) adapted to engage a needless syringe (not shown). In operation, the user engages the water seal access port 29 with the syringe in order to remove excess water seal 30 or add more water seal 30 to the water seal chamber 16.

It should be understood from the foregoing that, while particular embodiments of the invention have been illustrated and described, various modifications can be made thereto without departing from the spirit and scope of the present invention. Therefore, it is not intended that the invention be limited by the specification; instead, the scope of the present invention is intended to be limited only by the appended claims.

I claim:

1. A medical drainage device comprising:
   a casing, said casing defining a collection chamber therein for receiving fluid to be drained from a patient, and
   a vacuum regulator in communication with said collection chamber for limiting the amount of vacuum applied to said collection chamber, said vacuum regulator including a housing having an adjustable knob that extends outwardly from said housing and which operates to adjust the level of vacuum applied to the collection chamber, said adjustable knob having a slanted surface with a plurality of vacuum setting indicia thereon and an arrow for indicating the degree of vacuum being applied to said collection chamber.

2. The medical drainage device according to claim 1, wherein said arrow is raised above said housing.

3. The medical drainage device according to claim 1, wherein said housing extends outwardly from said casing.

4. The medical drainage device according to claim 1, wherein said casing has a top and bottom portions, front and back portions, and opposing side portions.

5. The medical drainage device according to claim 4, wherein said housing is located along said top portion of said casing.

6. The medical drainage device according to claim 1, wherein said slanted surface of said adjustable knob permits viewing from either the top or side of said casing.

7. The medical drainage device according to claim 1, wherein said adjustable knob includes an arrow for indicating the direction said regulator control knob is being rotated.

8. The medical drainage device according to claim 7, wherein said arrow is textured for clearer viewing.

9. A medical drainage device comprising:
   a casing, said casing including a collection chamber therein for receiving fluid to be drained from a patient, and
   a vacuum regulator in communication with said collection chamber for limiting the amount of vacuum applied to said collection chamber, and
   a vacuum indicator assembly in communication with said collection chamber, said vacuum indicator assembly including a raised base, and a recess comprising a surface, said vacuum indicator assembly further including a means for indicating the presence of vacuum in said collection chamber, said vacuum indicator assembly including a collapsible thimble engaged over said raised base, wherein said collapsible thimble forms a pocket with said recess which masks a symbol when vacuum is absent from said collection chamber.

10. The medical drainage device according to claim 9, wherein said collapsible thimble collapses over said symbol when vacuum is applied to said collection chamber.

11. The medical drainage device according to claim 10, wherein said symbol is unmasked when said collapsible thimble covers said symbol.

12. The medical drainage device according to claim 9, wherein said surface is slanted.

13. The medical drainage device according to claim 9, wherein said pocket communicates with said collection chamber through a hole formed through said surface.

14. The medical drainage device according to claim 9, wherein said collapsible thimble defines a section having an increased thickness relative to a remainder of said collapsible thimble.

15. The medical drainage device according to claim 9, wherein said base further defines an insert portion formed adjacent an extension member and a cover for encasing said thimble and said base.

16. The medical drainage device according to claim 9, wherein said collapsible thimble comprises a body having a slanted surface at one end and a flange formed at the other end thereof.

17. A medical drainage device comprising:
- a casing, said casing defining a collection chamber therein for receiving fluid drained from a patient, and
- a vacuum regulator in communication with said collection chamber for limiting the degree of vacuum applied to said collection chamber; and
- a vacuum indicator assembly in communication with said collection chamber, said vacuum indicator assembly including a raised base defining an extension member forming a recess at the free end thereof, said recess including a surface having a symbol for indicating the presence of vacuum inside said collection chamber, said vacuum indicator assembly further including a means for selectively masking and unmasking said symbol for indicating the absence or presence of vacuum to said collection chamber.

18. A vacuum indicator for a medical drainage device comprising:
- a raised base extending outwardly from the medical drainage device, said raised base defining an extension member forming a recess, said recess including a slanted surface having a symbol;
- a collapsible thimble engageble with said extension member, said thimble operable between a first position when vacuum is absent in the medical drainage device, and a second position when vacuum is present in the medical drainage device.

19. The vacuum indicator according to claim 18, wherein said symbol is masked from view by said thimble when said thimble is in the first position.

20. The vacuum indicator according to claim 18, wherein said symbol is exposed to view by said thimble when said thimble is in said second position.

21. The vacuum indicator according to claim 20, wherein said thimble collapses over said symbol when said thimble is in said second position.

22. The vacuum indicator according to claim 18, wherein said symbol is viewable from more than one direction when said thimble is in said second position.

23. The vacuum indicator according to claim 18, wherein said thimble forms a pocket with said recess when said thimble is in said first position such that said symbol is masked from view.

24. The vacuum indicator according to claim 23, wherein said thimble collapses said pocket and over said slanted surface when said thimble is in said second position such that said symbol is exposed to view through said thimble.

25. The vacuum indicator according to claim 18, wherein the vacuum indicator further comprises a cover for encasing said thimble and raised based.

26. The vacuum indicator according to claim 18, wherein said cover includes an alignment member for properly aligning said cover relative to said casing.

27. The vacuum indicator according to claim 18, wherein said thimble is semi-transparent.

* * * * *